United States Patent [19]
van der Aalst et al.

[11] Patent Number: 5,504,268
[45] Date of Patent: Apr. 2, 1996

[54] PROCESS FOR THE SELECTIVE HYDROGENATION OF AROMATIC ACETYLENE COMPOUNDS

[75] Inventors: Matheus J. M. van der Aalst, Terneuzen, Netherlands; Fernando A. de Benito, Madrid, Spain

[73] Assignee: The Dow Chemical Company, Midland, Mich.

[21] Appl. No.: 211,696

[22] PCT Filed: Oct. 10, 1991

[86] PCT No.: PCT/US91/07471

§ 371 Date: Apr. 8, 1994

§ 102(e) Date: Apr. 8, 1994

[87] PCT Pub. No.: WO93/07108

PCT Pub. Date: Apr. 15, 1993

[51] Int. Cl.$^6$ ........................................ C07C 5/10
[52] U.S. Cl. ................................ 585/259; 585/269
[58] Field of Search .......................... 585/259, 269

[56] References Cited

U.S. PATENT DOCUMENTS

| | | | |
|---|---|---|---|
| 4,389,517 | 6/1983 | Priddy et al. | 526/64 |
| 4,822,936 | 4/1989 | Maurer et al. | 589/259 |
| 5,156,816 | 10/1992 | Butler et al. | 422/141 |

FOREIGN PATENT DOCUMENTS 2603578  3/1988  France.

OTHER PUBLICATIONS

Patent Abstracts of Japan, vol. 11, No. 268 (C–444) (2715) 1987 & JP A 62 072 634 (Mitsubishi) 1987.
Research Disclosure No. 165, Jan. 1978, pp. 13–14; The Goodyear Tire & Rubber.
Chemical Abstract 110:173943c 1989.
J6 3280–032–A Abstract 1988.
Chemical Abstract 107:154904n 1987.
Chemical Abstract 108(11):94201q 1988.

*Primary Examiner*—Anthony Mc Farlane
*Assistant Examiner*—Bekir L. Yildirim

[57] ABSTRACT

A process for the selective hydrogenation of aromatic acetylene compounds present as impurities in vinyl-aromatic compounds without substantial loss of vinyl-aromatic compound comprises adding hydrogen and an inert gas to a liquid phase vinyl-aromatic compound containing aromatic acetylene compounds and contacting the aromatic acetylene compound with hydrogen in the presence of a selective hydrogenation catalyst, wherein the partial hydrogen pressure is from about 0.001 to about 0.05 bar.

13 Claims, No Drawings

PROCESS FOR THE SELECTIVE HYDROGENATION OF AROMATIC ACETYLENE COMPOUNDS

The present invention relates to a process for the selective hydrogenation of aromatic acetylene compounds present as impurities in vinyl-aromatic compounds comprising contacting the aromatic acetylene compound with hydrogen in the presence of a selective hydrogenation catalyst.

Aromatic acetylene compounds are common impurities in vinyl-aromatic compounds. For example, acetylenic compounds result as by-product in the production of vinyl-aromatic compounds by the dehydrogenation of ethyl-aromatic compounds. Excessive dehydrogenation leads to the highly unsaturated aromatic acetylene compounds. For example, in the production of styrene by dehydrogenation of ethylbenzene, phenylacetylene may be formed in amounts up to about 1,000 ppm. These acetylenic compounds are detrimental in the polymerization or copolymerization of the vinyl-aromatic compounds. The acetylenic impurities may lead to deactivation of the polymerization catalyst and to the formation of gels, such as, for example in the production of polymers or copolymers of styrene produced according to anionic or free radical polymerization techniques. It is thus desired to reduce the amounts of acetylenic compounds present in vinyl-aromatic compounds.

The vinyl-aromatic compound, however, contains a vinyl group which competes for hydrogenation with the acetylene group of the aromatic acetylene compound. Non-selective and excessive hydrogenation will therefore result in an undesired conversion of the vinyl-aromatic compound to the corresponding ethyl-aromatic compound, and thus cause loss of the desired product.

Japanese Patent Application No. 62-72633 discloses a method for the selective hydrogenation of impurities with a high degree of unsaturation which are present in styrenes, by carrying out the hydrogenation in at least two steps under conditions that in each step the molar ratio of hydrogen supplied to the reaction system to phenylacetylene is 10 or less, and preferably 5 to 1.5. As follows from the examples, the styrene still contains 50 ppm phenylacetylene, whereas the styrene loss was 0.02 percent.

In Japanese Patent Application No. 62-72634 a method for the purification of styrenes is disclosed by selectively hydrogenating the phenylacetylene present in the styrenes while the partial pressure of the hydrogen which is supplied to the reaction system is kept at 2 kg/cm$^2$ or less. From the examples it becomes clear that in order to achieve an acceptable phenylacetylene conversion a significant loss of styrene should be accepted.

According to the present invention aromatic acetylene compounds present as impurities in vinyl-aromatic compounds can be selectively hydrogenated to very low levels, and preferably to levels of about 10 ppm or less, without substantial loss of vinyl-aromatic compound.

The present invention provides a process for the selective hydrogenation of aromatic acetylene compounds present as impurities in vinyl-aromatic compounds comprising adding hydrogen and an inert gas to a liquid phase vinyl-aromatic compound containing an aromatic acetylene compound and contacting the aromatic acetylene compound with hydrogen in the presence of a selective hydrogenation catalyst, wherein the partial hydrogen pressure is from about 0.001 to about 0.05 bar.

It has been found that a highly selective hydrogenation can be achieved by having in the liquid phase a molar excess of the aromatic acetylene compound with respect to hydrogen. As the vinyl-aromatic compound concentration is much higher than that of the aromatic acetylene compound, whereas the latter compound adsorbs much stronger, both compounds compete for the active catalyst sites. The aromatic acetylene compound adsorbed on the active catalyst site is then hydrogenated to the vinyl-aromatic compound. It is important that the vinyl-aromatic compound before being released from the active catalyst site and being replaced by the much stronger adsorbing aromatic acetylene compound, has a low exposure to hydrogen in the liquid phase surrounding the catalyst. By limiting hydrogen availability in the liquid phase a highly selective hydrogenation process is obtained. By using an inert gas to lower the partial hydrogen pressure the amount of hydrogen dissolving in the liquid phase, can be lowered to the desired level. The relatively high partial hydrogen pressures used in the above-mentioned Japanese patent applications give large molar excesses of hydrogen in the liquid phase and accordingly can not achieve at the same time a very low aromatic acetylene compound concentration; for example, less than 10 ppm, and a very low loss of vinyl-aromatic compound; for example, less than 100 ppm.

A further advantage of the present process is that less hydrogen is consumed than in the prior art processes.

The vinyl-aromatic compounds which are purified according to the present process may comprise styrene and substituted styrenes; such as for examples, methyl and ethyl styrenes, divinyl benzenes, etc. Also mixtures of vinyl-aromatic compounds and saturated hydrocarbons may be purified according to the present process.

The aromatic acetylene impurities present in the vinyl-aromatic compounds are usually phenylacetylene and alkyl- or vinyl-substituted phenylacetylenes. These impurities may be present in amounts up to about 5,000 ppm, on a weight basis, depending on the way the vinyl-aromatic compounds is produced.

According to the present invention the partial hydrogen pressure preferably is from about 0.002 to about 0.01 bar.

The total pressure in the selective hydrogenation process is generally equal to or less than 5 bar, and preferably from about 1 to about 2 bar.

As inert gas to be used in the process of the present invention any gas can be used which does not in an adverse manner influence the conversion and selectivity rates of the present process. Suitable gasses are for example nitrogen, the noble gasses, and methane. Preferably the inert gas comprises nitrogen, methane or mixtures thereof. Preferably, the inert gas is first mixed with hydrogen and subsequently introduced into the reactor.

The process of the present invention is generally carried out at temperatures between 0° and 50° C., but more preferably at temperatures from 10° to 30° C. The temperature and pressure are selected in such a way as to maintain the vinyl-aromatic compound in the liquid phase and to prevent polymerization reactions.

In the process of the present invention any suitable selective hydrogenation catalyst can be used. Suitable catalysts comprise nickel, platinum, palladium, ruthenium and rhodium transition metals as catalyst components. These components usually are in the form of a salt, as a complex or in the form of a metal. Prior to or during their use, a reduction is carried out to produce the active catalyst component. These catalyst components may be present on a suitable carrier such as for example silica, alumina, aluminosilicates or other natural or synthetic inorganic carriers.

Preferably a palladium catalyst supported on an inert carrier material is used as selective hydrogenation catalyst. The inert carrier material is preferably alumina. When using a supported catalyst, the catalytically active component is usually present in an amount of 0.01 to 1 weight percent and preferably in an amount of 0.05 to 0.5 weight percent, based on the total catalyst weight.

The present process may be carried out in a batch mode or in a continuous flow mode. Preferably, the process is carried out in a continuous flow operation, more preferably in a continuous up-flow operation. Any type of batch or continuous flow reactor can be used in the present process. The catalyst is preferably used as a fixed catalyst bed.

The liquid hourly space velocity of the vinyl-aromatic compound is generally from 0.1 to 50 per hour, and preferably between 1 and 10 per hour.

When the vinyl-aromatic compound contains a relatively high amount of acetylenic impurities, it is advantageous to introduce hydrogen at more than one point along the direction of flow of the vinyl-aromatic compound, and between consecutive hydrogen introduction points the vinyl-aromatic compound containing the acetylenic impurities is contacted with catalyst In this mode of operation, the desired limited hydrogen concentration in the liquid phase can be maintained throughout the process even at relatively high aromatic acetylene compound concentrations.

According to a further aspect the present invention relates to the use of the vinyl-aromatic compound purified according to the process of any of the preceding claims in free radical or anionic polymerization or copolymerization techniques. In this way improved catalyst lifetimes can be achieved as well as polymerization products having very low gel levels.

In the Examples given below all percentages and ppm (parts per million) values are expressed on a weight basis unless otherwise indicated. The phenylacetylene concentrations in the starting product and after the selective hydrogenation were determined by gas chromatography. The styrene loss in the experiments was determined by measuring the increase of ethylbenzene concentration by gas chromatography. In the Tables the abbreviations have the following meanings: PA is phenylacetylene; $pH_2$ is partial hydrogen pressure; LHSV is Liquid Hourly Space Velocity.

EXAMPLE 1

The experiments described in this Example show the influence of the partial hydrogen pressure on the styrene loss for a given final concentration of phenylacetylene.

To a stirred batch reactor containing 0.6 g of a palladium-on-alumina catalyst (0.3 percent palladium on γ-alumina), 300 ml styrene containing 94 ppm phenylacetylene was introduced. The catalyst was reduced under the reaction conditions. The temperature was maintained at 21° C. and the total pressure at 1 bar. For the experiments carried out by partial hydrogen pressures of less than 1 bar, the desired partial hydrogen pressure was adjusted by mixing hydrogen with varying amounts of nitrogen. The hydrogen or hydrogen/nitrogen mixture was added to the reactor by bubbling through the liquid phase. The reaction was allowed to proceed until a final phenylacetylene concentration of 5 ppm and 10 ppm, respectively, was obtained. The results are summarized in the following Table I. These experiments show that for rather low phenylacetylene concentrations in the styrene (94 ppm), according to the invention (run nos. 3, 4, 7 and 8), surprisingly low to no styrene losses (less than 100 ppm) are obtained at high phenylacetylene conversion levels (95 percent for 5 ppm outlet concentration and 89 percent for 10 ppm outlet concentrations). In run 8 even a gain in styrene is obtained as more phenylacetylene is converted to styrene than the amount of styrene converted to ethylbenzene.

TABLE I

| Run no. | PA concentration [ppm] | $pH_2$ [bar] | Styrene loss [ppm] |
|---|---|---|---|
| 1 (comparative) | 5 | 1 | 550 |
| 2 (comparative) | 5 | 0.25 | 370 |
| 3 | 5 | 0.025 | 80 |
| 4 | 5 | 0.01 | 0 |
| 5 (comparative) | 10 | 1 | 450 |
| 6 (comparative) | 10 | 0.25 | 330 |
| 7 | 10 | 0.025 | 50 |
| 8 | 10 | 0.01 | −10 |

EXAMPLE 2

The following experiments show the influence of the partial hydrogen pressure on the styrene loss and on the outlet concentration of phenylacetylene for a continuous flow operation.

To a continuous up-flow fixed catalyst bed reactor styrene containing 94 ppm phenylacetylene was fed. The catalyst used was the same as in Example I. The catalyst was reduced before starting the experiments by passing hydrogen through at 50° C. during 6 hours. The temperature was maintained at 23° C. and the total pressure at 2 bar. The molar ratio of hydrogen and phenylacetylene, both supplied to the reactor, was 23. The desired partial hydrogen pressure was adjusted by adjusting the flow of nitrogen introduced into the reactor. The results are summarized in Table II, which also gives the hydrogen consumption in ppm. These experiments show the very surprising results that are obtained according to the present invention (run nos. 2 and 3). Under otherwise identical conditions, lowering the partial hydrogen pressure to within the range prescribed by the present invention substantially reduces the styrene loss, whereas very high phenylacetylene conversion rates are obtained. The hydrogen consumption data show that in the comparative runs much more hydrogen was consumed than in the runs according to the invention, whereas the extra consumed hydrogen was used to convert styrene to ethylbenzene.

TABLE II

| Run no. | $pH_2$ [bar] | LHSV [h⁻¹] | PA conc. [ppm] | Styrene loss [ppm] | Hydrogen consumption [ppm] |
|---|---|---|---|---|---|
| 1 (comp.) | 2 | 6 | 9 | 2000 | 42 |
| 2 | 0.0075 | 6 | 2 | 44 | 4.4 |
| 3 | 0.0025 | 3 | 6 | 0 | 3.7 |

We claim:

1. A process for the selective hydrogenation of aromatic acetylene compounds present as impurities in vinyl-aromatic compounds comprising adding hydrogen and an inert gas to a liquid phase vinyl-aromatic compound containing an aromatic acetylene compound and contacting the aromatic acetylene compound with hydrogen in the presence of a selective hydrogenation catalyst, wherein the partial hydrogen pressure is from about 0.001 to about 0.05 bar.

2. The process of claim 1 wherein the partial hydrogen pressure is from about 0.002 to about 0.01 bar.

3. The process as in one of claims 1 or 2 wherein the total pressure is equal to or less than 5 bar.

4. The process of claim 3 wherein the total pressure is from about 1 to about 2 bar.

5. The process of claim 1 wherein the inert gas comprises nitrogen or methane or mixtures thereof.

6. The process of claim 1 wherein the temperature is from 0° to 50° C.

7. The process of claim 6 wherein the temperature is from 10° to 30° C.

8. The process of claim 1 wherein the selective hydrogenation catalyst is a palladium catalyst supported on an inert carrier material.

9. The process of claim 1 wherein the catalyst is used as a fixed catalyst bed in a continuous up-flow process.

10. The process of claim 9 wherein the liquid hourly space velocity is from 0.1 to 50 per hour.

11. The process of claim 9 wherein hydrogen is introduced at more than one point along the direction of flow of the vinyl-aromatic compound, and between consecutive hydrogen introduction points the vinyl-aromatic compound containing the acetylenic impurities is contacted with catalyst.

12. The process of claim 5 wherein the partial hydrogen pressure is from about 0.002 to about 0.01 bar.

13. The process of claim 8 wherein the partial hydrogen pressure is from about 0.002 to about 0.01 bar.

* * * * *